US009121853B2

(12) United States Patent
Kwon et al.

(10) Patent No.: US 9,121,853 B2
(45) Date of Patent: Sep. 1, 2015

(54) B7-H4 EXPRESSION ON TUMOR VASCULATURE

(75) Inventors: Eugene D. Kwon, Rochester, MN (US); John Cheville, Pine Island, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1835 days.

(21) Appl. No.: 11/688,638

(22) Filed: Mar. 20, 2007

(65) Prior Publication Data
US 2007/0218032 A1 Sep. 20, 2007

Related U.S. Application Data

(60) Provisional application No. 60/784,031, filed on Mar. 20, 2006.

(51) Int. Cl.
| | |
|---|---|
| G01N 33/574 | (2006.01) |
| A61K 39/395 | (2006.01) |
| C12N 15/113 | (2010.01) |
| A61K 38/19 | (2006.01) |
| A61K 38/39 | (2006.01) |
| A61K 38/48 | (2006.01) |

(52) U.S. Cl.
CPC .......... *G01N 33/57484* (2013.01); *A61K 38/19* (2013.01); *A61K 38/39* (2013.01); *A61K 38/484* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. et al. | |
| 4,034,074 A | 7/1977 | Miles | |
| 4,098,876 A | 7/1978 | Piasio et al. | |
| 4,233,402 A | 11/1980 | Maggio et al. | |
| 4,469,863 A | 9/1984 | T'so et al. | |
| 4,642,334 A | 2/1987 | Moore et al. | |
| 4,816,567 A | 3/1989 | Cabilly et al. | |
| 5,214,136 A | 5/1993 | Lin et al. | |
| 5,218,105 A | 6/1993 | Cook et al. | |
| 5,235,033 A | 8/1993 | Summerton et al. | |
| 5,296,347 A | 3/1994 | LaMotte, III | |
| 5,482,856 A | 1/1996 | Fell, Jr. et al. | |
| 5,565,332 A | 10/1996 | Hoogenboom et al. | |
| 5,596,086 A | 1/1997 | Matteucci et al. | |
| 5,750,666 A | 5/1998 | Caruthers et al. | |
| 6,054,297 A | 4/2000 | Carter et al. | |
| 6,808,901 B1 | 10/2004 | Neuberger et al. | |
| 6,891,030 B2 | 5/2005 | Chen | |
| 6,933,146 B2 | 8/2005 | Helliwell et al. | |
| 7,304,149 B2 * | 12/2007 | Murphy et al. | 536/23.5 |
| 8,609,816 B2 * | 12/2013 | Korman et al. | 530/387.1 |
| 2005/0163772 A1* | 7/2005 | Dong et al. | 424/141.1 |

OTHER PUBLICATIONS

Thompson et al. (Urology, vol. 66(Supp. 5A), pp. 10-14, Nov. 2005).*
Ichikawa et al. (Front. Bioscience, vol. 10, pp. 2856-2860, Sep. 2005) Abstract only.*
Drucker (Cancer Treatment Reviews, vol. 31, pp. 536-545, 2005).*
Thompson et al. PNAS, Dec. 7, 2004, vol. 101, No. 49, p. 17174-17179.*
Salceda et al (Experimental Cell Research, 2005, 306:128-141, online Mar. 2005).*
GenBank Accession No. AAP37283, dated Jun. 1, 2003, 2 pages.
GenBank Accession No. AY280972, dated Jun. 1, 2003, 2 pages.
Cheville et al., "Comparisons of Outcome and Prognostic Features Among Histologic Subtypes of Renal Cell Carcinoma," *Am. J. Surg. Pathol.*, 2003, 27(5):612-624.
Choi et al., "Genomic Organization and Expression Analysis of B7-H4, an Immune Inhibitory Molecule of the B7 Family," *J. Immunol.*, 2003, 171:4650-4654.
Cogoni and Macino, "Gene silencing in *Neurospora crassa* requires a protein homologous to RNA-dependent RNA polymerase," *Nature*, 1999, 399:166-169.
Cogoni et al., "Transgene silencing of the *al-1* gene in vegetative cells of *Neurospora* is mediated by a cytoplasmic effector and does not depend on DNA-DNA interactions or DNA methylation," *EMBO J.*, 1996, 15(12):3153-3163.
Cristiano and Roth, "Molecular conjugates: a targeted gene delivery vector for molecular medicine," *J. Mol. Med.*, 1995, 73:479-486.
Dong et al., "Tumor-associated B7-H1 promotes T-cell apoptosis: A potential mechanism of immune evasion," *Nature Med.*, 2002, 8(8):793-800.
Figlin et al., "Treatment of metastatic renal cell carcinoma with nephrectomy, interleukin-2 and cytokine-primed or CD8(+) selected tumor infiltrating lymphocytes from primary tumor," *J. Urol.*, 1997, 158:740-745.
Fire et al., "Potent and specific genetic interference by double-stranded RNA in *Caenorhabditis elegans*," *Nature*, 1998, 391:806-811.
Fyfe et al., "Results of Treatment of 255 Patients With Metastatic Renal Cell Carcinoma Who Received High-Dose Recombinant Interleukin-2 Therapy," *J. Clin. Oncol.*, 1995, 13(3):688-696.
Jemal et al., "Cancer statistics, 2005," *CA Cancer J. Clin.*, 2005, 55:10-30.
Kennerdell and Carthew, "Use of dsRNA-Mediated Genetic Interference to Demonstrate that frizzled and frizzled 2 Act in the Wingless Pathway," *Cell*, 1998, 95:1017-1026.
Kovacs et al., "The Heidelberg classification of renal cell tumours," *J. Pathol.*, 1997, 183:131-133.
Krambeck et al., "B7-H4 expression in renal cell carcinoma and tumor vasculature: Associations with cancer progression and survival," *Proc. Natl. Acad. Sci. USA*, 2006, 103(27):10391-10396.

(Continued)

*Primary Examiner* — Laura B Goddard
(74) *Attorney, Agent, or Firm* — Fish & Richardson P.C.

(57) ABSTRACT

Methods of evaluating patients by assessing expression of B7-H4 in the vasculature are described.

11 Claims, 1 Drawing Sheet

(56) References Cited

OTHER PUBLICATIONS

Leibovich et al., "Prediction of Progression after Radical Nephrectomy for Patients with Clear Cell Renal Cell Carcinoma. A Stratification Tool for Prospective Clinical Trials," *Cancer*, 2003, 97:1663-1671.

Misquitta and Paterson, "Targeted disruption of gene function in *Drosophila* by RNA interference (RNA-i): A role for *Nautilus* in embryonic somatic muscle formation," *Proc. Natl. Acad. Sci. USA*, 1999, 96:1451-1456.

Motzer et al., "Renal-cell carcinoma," *N. Engl. J. Med.*, 1996, 335(12):865-875.

Pantuck et al., "The changing natural history of renal cell carcinoma," *J. Urol.*, 2001, 166:1611-1623.

Romano and Macino, "Quelling: transient inactivation of gene expression in *Neurospora crassa* by transformation with homologous sequences," *Mol. Microbiol.*, 1992, 6(22):3343-3353.

Störkel et al., "Classification of Renal Cell Carcinoma: Workgroup No. 1. Union Internationale Contre le Cancer (UICC) and the American Joint Committee on Cancer (AJCC)," *Cancer*, 1997, 80(5):987-989.

Tringler et al., "B7-H4 Is Highly Expressed in Ductal and Lobular Breast Cancer," *Clin. Cancer Res.*, 2005, 11:1842-1848.

\* cited by examiner

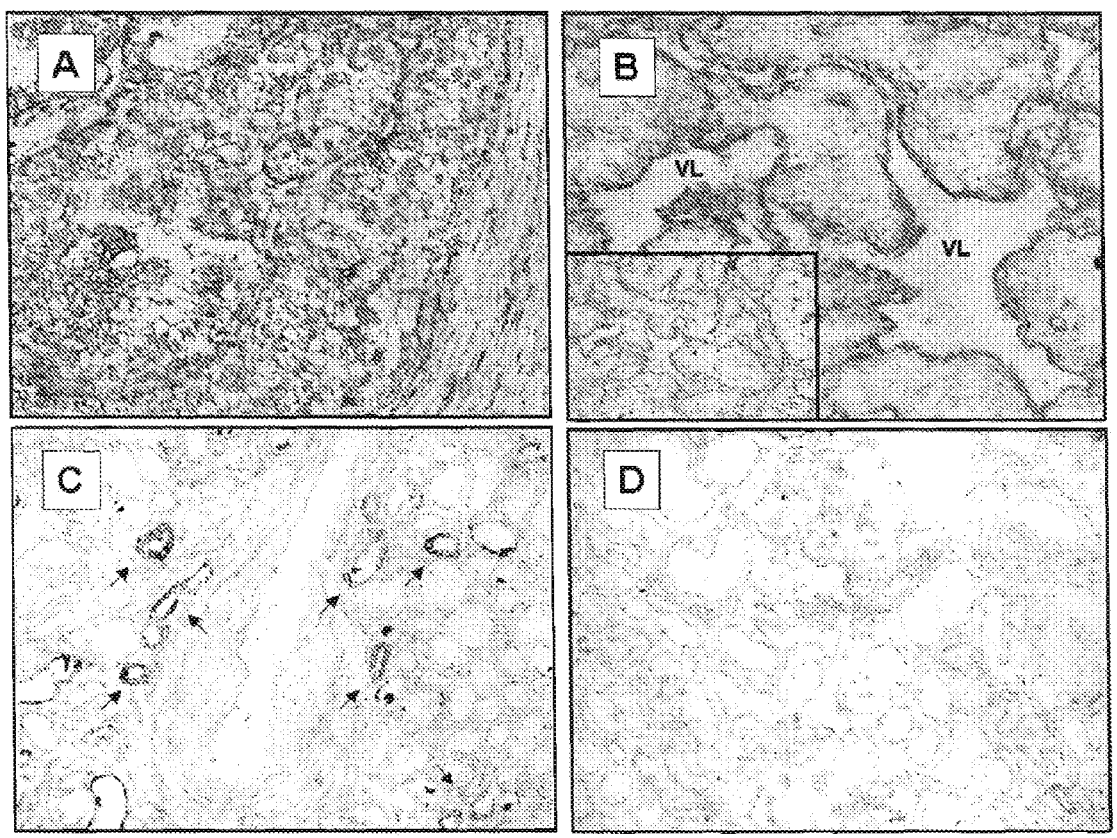

B7-H4 EXPRESSION ON TUMOR VASCULATURE

CROSS-REFERENCE TO RELATED APPLICATIONS

This application claims priority from U.S. Provisional Application Ser. No. 60/784,031, filed Mar. 20, 2006.

TECHNICAL FIELD

This document relates to expression of B7-H4 in biological samples, and more particularly, to evaluating patients based on the presence or absence of expression of B7-H4 in the vasculature.

BACKGROUND

The incidence of renal cell carcinoma (RCC) has increased steadily over the last three decades and the mortality rates continue to rise. See Jemal et al. (2005) *CA Cancer J. Clin.* 55, 10-30. To date the only acceptable treatment for clinically localized RCC is surgical extirpation. Improvements in imaging technology have led to a stage migration and with accompanying surgical advancements, improvements in patient survival have been noted. Pantuck et al. (2001) *J. Urol.* 166, 1611-1623. The five-year survival of RCC patients is still unacceptably low, however. The low survival rate reflects the 30% of patients who present with metastatic disease and another 25-30% who will subsequently develop disseminated disease after surgical excision of the primary tumor. Motzer et al. (1996) *N. Engl. J. Med.* 335, 865-875; and Leibovich et al. (2003) *Cancer.* 97, 1663-1671. Other treatment modalities for advanced disease, such as chemotherapy and radiation, have not been shown to be effective. Immunotherapy is an available adjunct therapy, but less than 10% of patients benefit with durable responses. Fyfe et al. (1995) *J. Clin. Oncol.* 13, 688-696. Limited therapeutic options have done little to improve the median survival of 6-10 months seen in metastatic disease. Figlin et al. (1997) *J. Urol.* 158, 740-750. Thus, there is a need for additional therapeutic targets for treatment of RCC.

SUMMARY

This document is based in part on the discovery that B7-H4 is expressed in the vasculature of tumors. As B7-H4 impairs T-cell function, detecting vasculature expression of B7-H4 can help discriminate between patients likely to benefit from IL-2 immunotherapy versus alternate forms of systemic therapy. Furthermore, since B7-H4 may contribute to tumorigenesis by acting at sites somewhat distant to the tumor cells themselves, tumor vasculature expression of B7-H4 provides a target for therapy.

In one aspect, the present document features a method of evaluating a subject (e.g., a renal cell carcinoma patient). The method can include assessing in a tissue sample from the subject the level of B7-H4 expression in the vasculature. The method can further comprise (a) if the tissue sample exhibits increased B7-H4 expression in the vasculature relative to a control level of B7-H4 expression, classifying the subject as having a relatively more aggressive cancer as compared to a subject having a corresponding tissue sample that does not exhibit increased B7-H4 expression in the vasculature relative to the control level of B7-H4 expression; or (b) if the tissue sample does not exhibit increased B7-H4 expression in the vasculature relative to the control level of B7-H4 expression, classifying the subject as not having a relatively more aggressive cancer as compared to a subject having a corresponding tissue sample that exhibits increased B7-H4 expression in the vasculature relative to the control level of B7-H4 expression. The control level of B7-H4 expression can be a level of B7-H4 expression in a non-cancerous tissue sample. The method can further comprise: (a) if the tissue sample exhibits no B7-H4 expression in the vasculature, classifying the subject as being more likely to benefit from IL-2 therapy than a subject having a tissue sample that exhibits B7-H4 expression in the vasculature; or, (b) if the tissue sample exhibits B7-H4 expression in the vasculature, classifying the subject as not being more likely to benefit from IL-2 therapy. Expression can be assessed by detecting the presence or absence of polypeptide. Detecting can include contacting the tissue sample with an antibody (e.g., a fluorescently labeled antibody) that binds to B7-H4. Detecting can include fluorescence flow cytometry (FFC) or immunohistochemistry. The tissue sample can be selected from the group consisting of lung, epithelial, connective, vascular, muscle, nervous, skeletal, lymphatic, prostate, cervical, breast, spleen, gastric, intestinal, oral, esophageal, dermal, liver, bladder, thyroid, thymic, adrenal, brain, gallbladder, pancreatic, uterine, ovarian, and testicular tissue. Renal tissue is particularly useful. The absence of expression of B7-H4 in the vasculature of the tissue sample can indicate the patient is more likely to benefit from IL-2 therapy.

This document also features a method of reducing B7-H4 activity (decreased $CD4^+$ and $CD8^+$ T cell proliferation). The method can include identifying a patient (e.g., a renal cell carcinoma patient) wherein B7-H4 is expressed in the tumor vasculature of the patient; and delivering to the patient an agent that reduces B7-H4 activity. The agent can include an antibody or a fragment thereof (e.g., an Fab' fragment, an $F(ab')_2$ fragment, or a single chain Fv (scFv) fragment). The agent can bind to B7-H4. The method further can include delivering to the patient one or more immunomodulatory cytokines, growth factors, or anti-angiogenic factors. The one or more immunomodulatory cytokines, growth factors, or anti-angiogenic factors can be selected from the group consisting of interleukin (IL)-1 to 25, interferon-alpha (IFN-α), interferon-beta (IFN-β), interferon-gamma (IFN-γ), tumor necrosis factor-alpha (TNF-α), granulocyte macrophage colony stimulating factor (GM-CSF), endostatin, angiostatin, and thrombospondin. The patient can have a cancer selected from the group consisting of hematological cancer, neurological cancer, melanoma, breast cancer, lung cancer, head and neck cancer, gastrointestinal cancer, liver cancer, pancreatic cancer, renal cancer, genitourinary cancer, bone cancer, and vascular cancer. In one embodiment, the agent is an antisense oligonucleotide that hybridizes to a B7-H4 transcript. In another embodiment, the agent is an interference RNA (RNAi).

In another aspect, this document features a method of evaluating a patient with renal cell carcinoma. The method can include assessing in a tissue sample from the patient the presence or absence of expression of B7-H4 in the vasculature. The method can further comprise, in the absence of expression of B7-H4 in the vasculature of said tissue sample, classifying said patient as being more likely to benefit from IL-2 therapy than if B7-H4 expression is present in the vasculature of said tissue sample. Expression can be assessed by detecting the presence or absence of polypeptide. Detecting can include contacting the tissue sample with an antibody (e.g., a fluorescently labeled antibody) that binds to B7-H4.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention will be apparent from the following description, from the drawing and from the claims.

DESCRIPTION OF DRAWING

FIG. 1A-1D are photomicrographs of RCC tumor specimens stained immunohistochemically for B7-H4. FIG. 1A is a photomicrograph of a representative RCC tumor specimen with strong membranous tumor cell and vascular B7-H4 immunohistochemical staining. FIG. 1B is a photomicrograph of a RCC tumor specimen with negative tumor cell, but positive vascular B7-H4 endothelial staining ("VL" denotes vascular lumen). The inset of FIG. 1B is a low-power, wide view photomicrograph of same tissue section. FIG. 1C is a photomicrograph of normal tumor-adjacent kidney specimen with focal and sporadic B7-H4 staining of the distal convoluted renal tubules (depicted by arrows). FIG. 1D is a photomicrograph of a normal tumor-adjacent kidney specimen with no B7-H4 staining. All photomicrographs ×400.

DETAILED DESCRIPTION

In general, methods and materials for evaluating patients for the presence or absence of expression of B7-H4 in the vasculature are provided. As used herein, the term "B7-H4" refers to B7-H4 from any mammalian species and the term "hB7-H4" refers to human B7-H4. B7-H4 also has been previously referred to as B7x or B7S1. Further details on B7-H4 polypeptides and nucleic acids are provided in U.S. Pat. No. 6,891,030, the disclosure of which is incorporated herein by reference in its entirety. The nucleotide and amino acid sequences of a hB7-H4 can be found in GenBank under Accession Nos. AY280972 and AAP37283, respectively. B7-H4 delivers an inhibitory signal to T cells, thereby abrogating $CD4^+$ and $CD8^+$ T cell proliferation, cell-cycle progression, and IL-2 production.

B7-H4 is a cell-surface glycoprotein and is anchored to the cytoplasmic membrane via a glycosyl phosphatidylinositol (GPI) linkage. B7-H4 polypeptide expression is primarily restricted to activated T cells, B cells, monocytes, and dendritic cells. While B7-H4 mRNA appears to be constitutively expressed in most tissues, expression of the polypeptide appears to be tightly controlled as B7-H4 polypeptide is not detected in most normal human tissues with sporadic expression detected in distal convoluted tubules of the kidney, ductal and acinar cells of the pancreas, endometrial glands, transitional epithelium of the ureter and bladder, bronchial epithelium of the lung, and columnar epithelium of the gallbladder. See Tringle et al. (2005) *Clin. Cancer Res.* 11:1842-1848. B7-H4 polypeptide has been detected, for example, in ovarian, breast, and lung cancers. See, Choi et al. (2003) *J. Immunol.* 171:4650-4655.

Methods of Evaluating Patients

In general, the methods provided herein include assessing the expression of B7-H4 in the vasculature of a tissue sample from a subject. Suitable subjects can be mammals, including, for example, humans, non-human primates such as monkeys, baboons, or chimpanzees, horses, cows (or oxen or bulls), pigs, sheep, goats, cats, rabbits, guinea pigs, hamsters, rats, gerbils, and mice. A "tissue sample" is a sample that contains cells or cellular material. Typically, the tissue sample is from a tumor, e.g., a resection or biopsy of a tumor.

As described herein, 81.5% of tumors examined expressed B7-H4 within the endothelium of the tumor vasculature. In contrast, only 6.5% of tumor-adjacent "normal" renal vessels were observed to express B7-H4, and such vessels may in fact represent either efferent or afferent vessels feeding the tumor. As such, detecting vasculature expression of B7-H4 can be useful for evaluating a subject (e.g., a human patient) and provide valuable clues as to course of action to be undertaken in treatment of the cancer and to the prognosis of the patient, since expression of B7-H4 indicates a particularly aggressive course of cancer. For example, evaluating a patient for the presence or absence of B7-H4 expression in the tumor vasculature can be used to determine if a patient is likely to benefit from immunotherapy. As B7-H4 impairs T-cell function by limiting T cell proliferation, the absence of B7-H4 tumor vasculature expression indicates a patient is more likely to benefit from systemic IL-2 immunotherapy than a patient where B7-H4 expression is present in the tumor vasculature.

In some embodiments, the level of B7-H4 expression in tissue from a subject can be compared to a control level of B7-H4 expression in, for example, (a) a tissue from the subject known not be cancerous (e.g., a contralateral kidney or lung, normal tissue surrounding or adjacent to a tumor, or an uninvolved lymph node); or (b) a corresponding tissue from one or more other subjects known not to have the cancer of interest, or known not to have any cancer. Thus, B7-H4 expression in the vasculature of a sample (e.g., a tumor sample) can be considered to be "increased" or "elevated" relative to B7-H4 expression in the vasculature of a control tissue sample if, for example, a greater number of tumor vasculature cells than control vasculature cells are positive for B7-H4.

The methods are applicable to a variety of cancers, including, for example, renal cancer, hematological cancer (e.g., leukemia or lymphoma), neurological cancer, melanoma, breast cancer, lung cancer, head and neck cancer, gastrointestinal cancer, liver cancer, pancreatic cancer, genitourinary cancer, bone cancer, and vascular cancer. As such, suitable tissue samples for assessing B7-H4 expression can include, for example, lung, epithelial, connective, vascular, muscle, nervous, skeletal, lymphatic, prostate, cervical, breast, spleen, gastric, intestinal, oral, esophageal, dermal, liver, bladder, thyroid, thymic, adrenal, brain, gallbladder, pancreatic, uterine, ovarian, and testicular tissue. Renal, breast, ovarian, and lung tissue samples are particularly useful for evaluating a patient with RCC, breast, ovarian, or lung cancer, respectively.

Typically, the presence or absence of B7-H4 expression is determined based on polypeptide expression. As used herein, with respect to B7-H4 and polypeptide expression, the term "presence" indicates that ≥5% of the cells in the tissue sample have detectable levels of B7-H4 polypeptide and the term "absence" indicates that <5% of the cells have detectable levels of B7-H4 polypeptide. In some embodiments, expression can be based on mRNA. In other embodiments, the level of expression of B7-H4 in tissue from a subject can be expressed relative to the expression of B7-H4 from (a) a tissue of a subject known not be cancerous (e.g., a contralateral kidney or lung, or an uninvolved lymph node); or (b) a corresponding tissue from one or more other subjects known not to have the cancer of interest, preferably known not to have any cancer.

Methods of detecting expression of a polypeptide in a tissue sample are known in the art. For example, antibodies that bind to an epitope specific for B7-H4 can be used to assess for the presence or absence of B7-H4 expression. As used herein, the terms "antibody" or "antibodies" include intact molecules (e.g., polyclonal antibodies, monoclonal antibodies, humanized antibodies, or chimeric antibodies) as well as fragments thereof (e.g., single chain Fv antibody fragments, Fab fragments, and F(ab)$_2$ fragments) that are capable of binding to an epitopic determinant of B7-H4 (e.g., hB7-H4). A scFv fragment is a single polypeptide chain that includes both the heavy and light chain variable regions of the antibody from which the scFv is derived. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). Polyclonal antibodies are heterogeneous populations of antibody molecules that are contained in the sera of the immunized animals. Monoclonal antibodies are homogeneous populations of antibodies to a particular epitope of an antigen.

Antibody fragments that can bind to B7-H4 can be generated by known techniques. For example, F(ab')$_2$ fragments can be produced by pepsin digestion of the antibody molecule; Fab fragments can be generated by reducing the disulfide bridges of F(ab')$_2$ fragments. Alternatively, Fab expression libraries can be constructed. See, for example, Huse et al., *Science,* 246:1275 (1989). scFv fragments can be produced, for example, as described in U.S. Pat. No. 4,642,334. Once produced, antibodies or fragments thereof are tested for recognition of B7-H4 by standard immunoassay methods including ELISA techniques, radioimmunoassays, and Western blotting. See, *Short Protocols in Molecular Biology,* Chapter 11, Green Publishing Associates and John Wiley & Sons, Edited by Ausubel, F. M. et al., 1992.

Antibodies having specific binding affinity for B7-H4 can be produced through standard methods. See, for example, Dong et al. (2002) *Nature Med.* 8:793-800. In general, a B7-H4 polypeptide can be recombinantly produced, or can be purified from a biological sample, and used to immunize animals. As used herein, the term "polypeptide" refers to a polypeptide of at least five amino acids in length. To produce a recombinant B7-H4 polypeptide, a nucleic acid sequence encoding the appropriate polypeptide can be ligated into an expression vector and used to transform a bacterial or eukaryotic host cell. Nucleic acid constructs typically include a regulatory sequence operably linked to a B7-H4 nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express a B7-H4 polypeptide can be produced by using expression vectors with the appropriate control elements and a selectable marker. For example, the eukaryotic expression vector pCDNA.3.1+ (Invitrogen, San Diego, Calif.) can be used to express a B7-H4 polypeptide in, for example, COS cells, Chinese hamster ovary (CHO), or HEK293 cells. Following introduction of the expression vector by electroporation, DEAE dextran, or other suitable method, stable cell lines can be selected. Alternatively, B7-H4 can be transcribed and translated in vitro using wheat germ extract or rabbit reticulocyte lysate.

In eukaryotic host cells, a number of viral-based expression systems can be utilized to express a B7-H4 polypeptide. A nucleic acid encoding a B7-H4 polypeptide can be introduced into a SV40, retroviral or vaccinia based viral vector and used to infect host cells. Alternatively, a nucleic acid encoding a B7-H4 polypeptide can be cloned into, for example, a baculoviral vector and then used to transfect insect cells.

Various host animals can be immunized by injection of the B7-H4 polypeptide. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin and dinitrophenol. Monoclonal antibodies can be prepared using a B7-H4 polypeptide and standard hybridoma technology. In particular, monoclonal antibodies can be obtained by any technique that provides for the production of antibody molecules by continuous cell lines in culture such as described by Kohler, G. et al., *Nature,* 256:495 (1975), the human B-cell hybridoma technique (Kosbor et al., *Immunology Today,* 4:72 (1983); Cole et al., *Proc. Natl. Acad. Sci USA,* 80:2026 (1983)), and the EBV-hybridoma technique (Cole et al., "The EBV-hybridoma Technique and its Application to Human Lung Cancer," in *Monoclonal Antibodies and Cancer Therapy,* Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies provided herein can be cultivated in vitro and in vivo.

In immunological assays, an antibody having specific binding affinity for B7-H4 or a secondary antibody that binds to such an antibody can be labeled, either directly or indirectly. Suitable labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, fluorescein-5-isothiocyanate (FITC), PerCP, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. In embodiments in which antibodies to B7-H4 are used in combination, the antibodies can be labeled such that each can be distinctly visualized (e.g., by labeling with two different fluorescent moieties). Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting B7-H4 can be performed in a variety of known formats, including sandwich assays (e.g., ELISA assays, sandwich Western blotting assays, or sandwich immunomagnetic detection assays), competition assays (competitive RIA), or bridge immunoassays. See, for example, U.S. Pat. Nos. 5,296,347; 4,233,402; 4,098,876; and 4,034,074. Some polypeptide-detecting assays (e.g., ELISA or Western blot) can be applied to lysates of cells, and others (e.g., immunohistological methods or fluorescence flow cytometry) can be applied to histological sections or unlysed cell suspensions.

Methods of detecting an mRNA in a tissue sample are known in the art. For example, cells can be lysed and an mRNA in the lysates or in RNA purified or semi-purified from the lysates can be detected by any of a variety of methods including, without limitation, hybridization assays using detectably labeled gene-specific DNA or RNA probes (e.g., Northern Blot assays) and quantitative or semi-quantitative RT-PCR methodologies using appropriate gene-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of Reducing B7-H4 Activity

The methods provided herein also can include identifying a subject where B7-H4 is expressed in the tumor vasculature of the subject and delivering to the subject (e.g., a human patient) one or more agents that reduce B7-H4 activity. B7-H4 delivers an inhibitory signal to T cells, thereby abrogating $CD4^+$ and $CD8^+$ T cell proliferation, cell-cycle progression, and IL-2 production. Since aberrant B7-H4 expression impairs T-cell function, reducing activity of B7-H4 (i.e., reducing the inhibition of T-cell function) can improve a patient's anti-tumor immune response. Thus, reducing B7-H4 activity can be used for the treatment of cancer, and in particular, renal cell carcinoma. The term "treatment" refers to complete abolishment of the symptoms or a decrease in the severity of the symptoms of the disease. In some embodiments, an agent can be administered prophylactically in subjects at risk for developing cancer to prevent development, delay onset, or lessen the severity of subsequently developed disease symptoms. In either case, an effective amount of an agent that reduces B7-H4 activity is administered to the subject. An "effective amount" of an agent is an amount of the agent that is capable of producing a medically desirable result in a treated subject without inducing clinically unacceptable toxicity to the host. The method can be performed alone or in conjunction with other drugs or therapy (e.g., chemotherapy or radiation).

Suitable agents include, for example, a drug, small molecule, an antibody or an antibody fragment, such as a Fab' fragment, a $F(ab')_2$ fragment, or a scFv fragment that binds B7-H4, an antisense oligonucleotide, an interfering RNA (RNAi), or combinations thereof. Methods for producing antibodies and antibody fragments are described above. Chimeric antibodies and humanized antibodies made from non-human (e.g., mouse, rat, gerbil, or hamster) antibodies also are useful. Chimeric and humanized monoclonal antibodies can be produced by recombinant DNA techniques known in the art, for example, using methods described in U.S. Pat. Nos. 4,816,567; 5,482,856; 5,565,332; 6,054,297; and 6,808, 901.

Antisense oligonucleotides as provided herein are at least 8 nucleotides in length and hybridize to a B7-H4 transcript. For example, a nucleic acid can be about 8, 9, 10-20 (e.g., 11, 12, 13, 14, 15, 16, 17, 18, 19, or 20 nucleotides in length), 15 to 20, 18-25, or 20-50 nucleotides in length. In other embodiments, antisense molecules can be used that are greater than 50 nucleotides in length, including the full-length sequence of a B7-H4 mRNA. As used herein, the term "oligonucleotide" refers to an oligomer or polymer of ribonucleic acid (RNA) or deoxyribonucleic acid (DNA) or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863; 5,235,033; 5,750,666; and 5,596,086 for methods of preparing oligonucleotides with modified backbones.

Antisense oligonucleotides also can be modified by chemical linkage to one or more moieties or conjugates that enhance the activity, cellular distribution or cellular uptake of the oligonucleotide. Such moieties include but are not limited to lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

Methods for synthesizing antisense oligonucleotides are known, including solid phase synthesis techniques. Equipment for such synthesis is commercially available from several vendors including, for example, Applied Biosystems (Foster City, Calif.). Alternatively, expression vectors that contain a regulatory element that directs production of an antisense transcript can be used to produce antisense molecules.

Antisense oligonucleotides can bind to a nucleic acid encoding B7-H4, including DNA encoding B7-H4 RNA (including pre-mRNA and mRNA) transcribed from such DNA, and also cDNA derived from such RNA, under physiological conditions (i.e., physiological pH and ionic strength). For example, an antisense oligonucleotide can hybridize under physiological conditions to the nucleotide sequence set forth in GenBank Accession No. AY280972.

It is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the B7-H4 nucleic acid interferes with the normal function of the B7-H4 nucleic acid, and non-specific binding to non-target sequences is minimal.

Target sites for B7-H4 antisense oligonucleotides include the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a B7-H4 nucleic acid can be evaluated by measuring levels of the B7-H4 mRNA or polypeptide (e.g., by Northern blotting, RT-PCR, Western blotting, ELISA, or immunohistochemical staining).

Double-stranded interfering RNA (RNAi) homologous to B7-H4 DNA can also be used to reduce expression of B7-H4 and consequently, activity of B7-H4. See, e.g., U.S. Pat. No. 6,933,146; Fire et al. (1998) *Nature* 391:806-811; Romano and Masino (1992) *Mol. Microbiol.* 6:3343-3353; Cogoni et al. (1996) *EMBO J.* 15:3153-3163; Cogoni and Masino (1999) *Nature* 399:166-169; Misquitta and Paterson (1999) *Proc. Natl. Acad. Sci. USA* 96:1451-1456; and Kennerdell and Carthew (1998) *Cell* 95:1017-1026.

The sense and anti-sense RNA strands of RNAi can be individually constructed using chemical synthesis and enzymatic ligation reactions using procedures known in the art. For example, each strand can be chemically synthesized using naturally occurring nucleotides or nucleic acid analogs. The sense or anti-sense strand also can be produced biologically using an expression vector into which a target B7-H4 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to the tumor vasculature or to tumor cells.

In one embodiment, the agent (e.g., drug, small molecule, antibody, antibody fragment, antisense oligonucleotide, interfering RNA) itself is administered to a subject. Generally, the agent will be suspended in a pharmaceutically-acceptable carrier (e.g., physiological saline) and administered orally or by intravenous (i.v.) infusion, or injected subcutaneously, intramuscularly, intrathecally, intraperitoneally, intrarectally, intravaginally, intranasally, intragastrically, intratracheally, or intrapulmonarily. The agent can, for example, be delivered directly to the affected organ or tissue and/or vasculature of the organ, or a site of an immune response such as a lymph node in the region of an affected tissue or organ or spleen. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100.0 mg/kg. Wide variations in the needed dosage are to be expected in view of the variety of compounds available and the differing efficiencies of various routes of administration. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a nucleic acid (e.g., an expression vector containing a regulatory sequence operably linked to a nucleic acid encoding the polypeptide, an expression vector containing a regulatory sequence operably linked to a nucleic acid encoding the antisense oligonucleotide, or an expression vector from which sense and anti-sense RNAs can be transcribed under the direction of separate promoters, or a single RNA molecule containing both sense and anti-sense sequences can be transcribed under the direction of a single promoter) can be delivered to appropriate cells in a subject. Suitable expression vectors include plasmids and viral vectors such as herpes viruses, retroviruses, vaccinia viruses, attenuated vaccinia viruses, canary pox viruses, adenoviruses and adeno-associated viruses, among others.

Expression of the nucleic acids can be directed to any cell in the body of the subject. However, it is particularly useful to direct expression to cells in, or close to, lymphoid tissue draining an affected tissue or organ. Expression of the nucleic acid can be directed, for example, to cells comprising the tumor vasculature, cancer tissue (e.g., tumor cells) or immune-related cells, e.g., B cells, macrophages/monocytes, or interdigitating dendritic cells. This can be achieved by, for example, the use of polymeric, biodegradable microparticle or microcapsule delivery devices known in the art and/or tissue or cell-specific antibodies. Alternatively, tissue specific targeting can be achieved by the use of tissue-specific transcriptional regulatory sequences (i.e., tissue specific promoter) which are known in the art.

Nucleic acids can be delivered to cells using liposomes, which can be prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73:479]. Delivery of "naked DNA" (i.e., without a delivery vehicle) to an intramuscular, intradermal, or subcutaneous site is another means to achieve in vivo expression.

Nucleic acids can be administered in a pharmaceutically acceptable carrier. Pharmaceutically acceptable carriers are biologically compatible vehicles that are suitable for administration to a human, e.g., physiological saline or liposomes. As discussed above, the dosage for any one patient depends upon many factors, including the patient's size, body surface area, age, the particular compound to be administered, sex, time and route of administration, general health, and other drugs being administered concurrently. Dosages will vary, but a preferred dosage for administration of nucleic acid is from approximately $10^6$ to approximately $10^{12}$ copies of the nucleic acid. This dose can be repeatedly administered, as needed. Routes of administration can be any of those described above.

In addition, the method can be an ex vivo procedure that involves providing a recombinant cell which is, or is a progeny of a cell, obtained from a subject and has been transfected or transformed ex vivo with one or more nucleic acids encoding one or more agents that reduce B7-H4 activity, so that the cell expresses the agent(s); and administering the cell to the subject. The cells can be cells obtained from a cancer tissue (e.g., tumor cells) or from a non-cancerous tissue obtained preferably from a subject to whom these cells are to be administered or from another subject. The donor and recipient of the cells can have identical major histocompatibility complex (MHC; HLA in humans) haplotypes. Optimally, the donor and recipient are homozygotic twins or are the same individual (i.e., are autologous). The recombinant cells can also be administered to recipients that have no, or only one, two, three, or four MHC molecules in common with the recombinant cells, e.g., in situations where the recipient is severely immunocompromised, where only mismatched cells are available, and/or where only short term survival of the recombinant cells is required or desirable.

The efficacy of an agent can be evaluated both in vitro and in vivo. Briefly, the agent can be tested for its ability, for example, to (a) reduce B7-H4 activity, (b) inhibit growth of cancer cells, (c) induce death of cancer cells, or (d) render the cancer cells more susceptible to cell-mediated immune responses generated by leukocytes (e.g., lymphocytes and/or macrophages). For in vivo studies, the agent can, for example, be injected into an animal (e.g., a mouse cancer model) and its effects on cancer are then assessed. Based on the results, an appropriate dosage range and administration route can be determined.

In some embodiments, one or more supplementary agents can be administered with an agent. Suitable supplementary agents include, for example, immunomodulatory cytokines, growth factors, anti-angiogenic factors, immunogenic stimuli, and/or antibodies specific for any of these. Such supplementary agents can administered before, simultaneous with, or after delivery of any of the above-listed agents.

Examples of immunomodulatory cytokines, growth factors, and anti-angiogenic factors include, without limitation, interleukin (IL)-1 to 25 (e.g., IL-2, IL-12, or IL-15), interferon-γ (IFN-γ), interferon-α (IFN-α), interferon-β (IFN-β), tumor necrosis factor-α (TNF-α), granulocyte macrophage colony stimulating factor (GM-CSF), endostatin, angiostatin, and thrombospondin. Immunomodulatory cytokines, growth factors, anti-angiogenic factors include substances that serve, for example, to inhibit infection (e.g., standard anti-microbial antibiotics), inhibit activation of T cells, or inhibit the consequences of T cell activation. For example, where it is desired to decrease a Th1-type immune response (e.g., in a delayed type hypersensitivity response), a cytokine such as interleukin (IL)-4, IL-10, or IL-13 or an antibody specific for a cytokine such as IL-12 or interferon-γ (IFN-γ) can be used. Alternatively, where it is desired to inhibit a Th2-type immune response (e.g., in an immediate type hypersensitivity response), a cytokine such as IL-12 or IFN-γ or an antibody specific for IL-4, IL-10, or IL-13 can be used as a supplementary agent. Also of interest are antibodies (or any of the above-described antibody fragments or derivatives) specific for proinflammatory cytokines and chemokines such as IL-1, IL-6, IL-8, TNF-α, macrophage inflammatory protein (MIP)-1, MIP-3α, monocyte chemoattractant protein-1 (MCP-1), epithelial neutrophil activating peptide-78 (ENA-78), interferon-γ-inducible protein-10 (IP10), Rantes, and any other appropriate cytokine or chemokine recited herein.

The invention will be further described in the following examples, which do not limit the scope of the invention described in the claims.

EXAMPLES

Example 1

Materials and Methods

Patient selection—Upon approval from the Mayo Clinic Institutional Review Board, 531 patients were identified from Mayo Clinic Nephrectomy Registry that were previously treated with radical nephrectomy or nephron-sparing surgery for unilateral, sporadic, non-cystic clear cell RCC between 2000 and 2003. Since pathologic features and patient outcome differ by RCC subtype, all analyses were restricted to patients treated with clear cell RCC only, the most common of the RCC subtypes [Cheville et al. (2003) *Am. J. Surg. Pathol.* 27:612-624]. In addition, patients were selected based on the availability of fresh-frozen tissue since the human B7-H4 specific monoclonal antibody (clone hH4.1) can reproducibly stain only fresh-frozen, not paraffin-fixed, tissue during immunohistochemical analysis.

Clinical and Pathologic features—The clinical features studied included age, sex, and symptoms. Patients with a palpable flank or abdominal mass, discomfort, gross hematuria, acute onset varicocele, or constitutional symptoms including rash, sweats, weight loss, fatigue, early satiety, and anorexia were considered symptomatic at presentation. The pathologic features studied included histologic subtype, tumor size, the 2002 primary tumor classification (T), regional lymph node involvement (N), distant metastases at nephrectomy (M), the 2002 TNM stage groupings, nuclear grade, coagulative tumor necrosis, and sarcomatoid differentiation. Histologic subtype was classified according to the Union Internationale Contre le Cancer, American Joint Committee on Cancer, and Heidelberg guidelines [Storkel et al. (1997) *Cancer* 80:987-989; and Kovacs et al. (1997) *J. Pathol.* 183:131-133]. These features were obtained by a review of the microscopic slides from all nephrectomy specimens by a urologic pathologist (J. C. C.), without knowledge of patient outcome.

B7-H4 Immunohistochemical Staining—Cryosections from RCC tumors (5 μm, −20° C.) were mounted on Superfrost Plus slides, air dried, and fixed in ice-cold acetone. Sections were stained using the Dako Autostainer and Dako Cytomation CSA II kit (Dako; Carpinteria, Calif.). Slides were blocked with $H_2O_2$ for five minutes followed by incubation with the antibody applied for 30 minutes at room temperature. Anti-mouse immunoglobulin-HRP then was applied at room temperature for 15 minutes followed by incubation with amplification reagent for 15 minutes. Slides then were incubated for 15 minutes with anti-fluorescein-HRP and visualized with DAB substrate for 8 minutes. Finally, sections were counter-stained for one minute with Hematoxylin. The antibody used for this protocol was the mouse anti-human B7-H4 monoclonal antibody (clone hH4.1). Human ovarian cancer tissue was used as a positive control. Irrelevant isotype-matched antibodies were used to control for non-specific staining.

Quantification of B7-H4 Expression—The percentages of tumor cells that stained positive for B7-H4 were quantified in 5% increments by a urologic pathologist (J. C. C.). The tumor was considered positive if there was histologic evidence of cell-surface membrane staining. Cases with <5% tumor staining were considered negative.

Statistical methods—Comparisons among the clinical and pathologic features were evaluated using chi-square and Fisher's exact tests. Overall, cancer-specific, and progression-free survival was estimated using the Kaplan-Meier method. The duration of follow-up was calculated from the date of surgery to the date of cancer progression (i.e., distant metastases), death, or last known follow-up. Cause of death was determined from death certificate or physician correspondence. The associations of B7-H4 tumor expression with death from any cause, death from RCC, and cancer progression was evaluated using Cox proportional hazards regression models univariately and after adjusting for the Mayo Clinic SSIGN (Stage, SIze, Grade, and Necrosis) Score, a prognostic composite score specifically developed for patients with clear cell RCC. These associations were summarized using risk ratios (RR) and 95% confidence intervals (95% CI). Statistical analyses were performed using the SAS software package (SAS Institute; Cary, N.C.). All tests were two-sided and p-values <0.05 were considered statistically significant.

Example 2

Survival of RCC Patients with Fresh-Frozen Tissue Samples Available

Of the 531 patients eligible for study, 259 (49%) had fresh-frozen tissue available for laboratory investigation. None of the clinical or pathologic features studied was significantly different between patients with and without fresh-frozen tissue available for study. Furthermore, there was not a statistically significant difference in overall survival (p=0.739) or cancer-specific survival (p=0.780) between the two groups.

At last follow-up, 63 of the 259 patients studied had died, including 47 patients who died from RCC at a median of 1.2 years following surgery (range 0-4.4). Among the 196 patients who were still alive at last follow-up, the median duration of follow-up was 2.6 years (range 0-5.6). Estimated overall survival rates (standard error [SE], number still at risk) at 1, 2, and 3 years following surgery were 90.3% (1.9%, 226), 79.7% (2.7%, 148), and 73.9% (3.1%, 88), respectively. Cancer-specific survival rates (SE, number still at risk) at the same time points were 92.1% (1.7%, 226), 83.5% (2.5%, 148), and 79.3% (2.9%, 88), respectively. Among the subset of 215 patients with clinically localized RCC at surgery (i.e., pNX/pN0, pM0), 36 progressed to distant metastases at a median of 1.1 years following surgery (range 0-4.9). Progression-free survival rates (SE, number still at risk) at 1, 2, and 3 years following surgery were 91.9% (1.9%, 187), 84.8% (2.6%, 125), and 81.5% (3.0%, 74), respectively.

Example 3

Tumor B7-H4 Expression

One hundred and fifty-three (59.1%) patient specimens exhibited positive tumor B7-H4 staining (FIG. 1A) with a median level of staining of 20% (range 5%-90%). A comparison of clinical and pathologic features by tumor B7-H4 expression is shown in Table 1. Positive tumor B7-H4 expression was associated with adverse clinical and pathologic features including the presence of constitutional symptoms, larger tumor size, higher tumor stage and grade, and tumor necrosis. For example, only one (0.9%) patient with a B7-H4-negative tumor had regional lymph node involvement compared with 14 (9.2%) patients with B7-H4-positive tumors (p=0.005).

Univariately, patients with B7-H4-positive tumors were over twice as likely to die from any cause compared with patients with B7-H4-negative tumors (risk ratio 2.51; 95% CI 1.42-4.45; p=0.002). The overall survival rate (SE, number still at risk) at 3 years following surgery for patients with B7-H4-positive tumors was 66.1% (4.5%, 43) compared with 84.5% (3.9%, 45) for patients with B7-H4-negative tumors. Patients with B7-H4-positive tumors were also significantly more likely to die from RCC (risk ratio 3.05; 95% CI 1.51-6.14; p=0.002). The 3-year cancer-specific survival rates (SE, number still at risk) for patients with B7-H4-positive and B7-H4-negative tumors were 71.2% (4.4%, 43) and 90.5% (3.0%, 45), respectively. After adjusting for the SSIGN

TABLE 1

Comparison of Pathologic Features by Tumor B7-H4 Expression

| | Tumor B7-H4 Expression | | |
|---|---|---|---|
| | Negative N = 106 | Positive N = 153 | |
| Feature | N (%) | | P-value |
| Age at Surgery (years) | | | |
| <65 | 55 (51.9) | 81 (52.9) | 0.867 |
| ≥65 | 51 (48.1) | 72 (47.1) | |
| Sex | | | |
| Female | 40 (37.7) | 45 (29.4) | 0.161 |
| Male | 66 (62.3) | 108 (70.6) | |
| Symptoms at Presentation | 49 (46.2) | 86 (56.2) | 0.114 |
| Constitutional Symptoms at Presentation | 9 (8.5) | 31 (20.3) | 0.010 |
| Primary Tumor Size (cm) | | | |
| <5 | 54 (50.9) | 48 (31.4) | <0.001 |
| 5 to <7 | 25 (23.6) | 28 (18.3) | |
| 7 to <10 | 12 (11.3) | 35 (22.9) | |
| ≥10 | 15 (14.2) | 42 (27.5) | |
| 2002 Primary Tumor Classification | | | |
| pT1a | 41 (38.7) | 40 (26.1) | 0.012 |
| pT1b | 32 (30.2) | 29 (19.0) | |
| pT2 | 11 (10.4) | 28 (18.3) | |
| pT3a | 10 (9.4) | 18 (11.8) | |
| pT3b | 11 (10.4) | 32 (20.9) | |
| pT3c | 1 (0.9) | 4 (2.6) | |
| pT4 | 0 (0.0) | 2 (1.3) | |
| Regional Lymph Node Involvement | | | |
| pNX/pN0 | 105 (99.1) | 139 (90.9) | 0.005 |
| pN1/pN2 | 1 (0.9) | 14 (9.1) | |
| Distant Metastases at Nephrectomy | | | |
| pM0 | 91 (85.9) | 128 (83.7) | 0.632 |
| pM1 | 15 (14.1) | 25 (16.3) | |
| 2002 TNM Stage Groupings | | | |
| I | 69 (65.1) | 68 (44.4) | 0.006 |
| II | 10 (9.4) | 20 (13.1) | |
| III | 12 (11.3) | 39 (25.5) | |
| IV | 15 (14.2) | 26 (17.0) | |

TABLE 1-continued

Comparison of Pathologic Features by Tumor B7-H4 Expression

| Feature | Tumor B7-H4 Expression | | P-value |
|---|---|---|---|
| | Negative N = 106 N (%) | Positive N = 153 | |
| Nuclear Grade | | | |
| 1 | 7 (6.6) | 6 (3.9) | <0.001 |
| 2 | 53 (50.0) | 33 (21.6) | |
| 3 | 42 (39.6) | 89 (58.2) | |
| 4 | 4 (3.8) | 25 (16.3) | |
| Coagulative Tumor Necrosis | 16 (15.1) | 57 (37.3) | <0.001 |
| Sarcomatoid Differentiation | 1 (0.9) | 7 (4.6) | 0.094 |

Score, patients with B7-H4-positive tumors were still nearly twice as likely to die from RCC, but this difference did not attain statistical significance (risk ratio 1.78; 95% CI 0.88-3.63; p=0.112). Among the subset of 215 patients with clinically localized RCC at surgery, patients with B7-H4-positive tumors were three times more likely to progress compared with patients with B7-H4-negative tumors (risk ratio 2.99; 95% CI 1.36-6.57; p=0.006). The 3-year progression-free survival rate (SE, number still at risk) for patients with B7-H4-positive tumors was 74.1% (4.5%, 34) compared with 91.2% (3.2%, 40) for patients with B7-H4-negative tumors.

Example 4

B7-H4 Expression in Tumor Vasculature

Two hundred and eleven (81.5%) cases exhibited B7-H4 endothelial expression within the tumor vasculature (FIG. 1B), with a median level of expression of 50% (range 5%-100%). Almost all (148/153; 96.7%) patients with B7-H4-positive tumors also exhibited B7-H4 endothelial staining within the tumor vasculature. Of the 106 patients with B7-H4-negative tumors, 63 (59.4%) exhibited B7-H4 endothelial staining within the tumor vasculature.

Tumor vasculature expression of B7-H4 also was assessed in 46 randomly selected patients from the 259 under study who had available fresh-frozen tissue from normal kidney adjacent to the tumor. Of these, only 3 (6.5%) specimens exhibited B7-H4 staining in the normal vasculature. Twenty-six (56.5%) specimens exhibited B7-H4 staining in the distal tubules (FIG. 1C), and the remaining demonstrated no B7-H4 staining (FIG. 1D).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing B7-H4 activity, said method comprising:
   (a) identifying a patient as having a tumor that is B7-H4 negative but that exhibits B7-H4 expression in the tumor vasculature; and
   (b) delivering to said patient an agent that reduces B7-H4 activity.

2. The method of claim 1, wherein said agent comprises an antibody or a fragment thereof.

3. The method of claim 2, wherein said antibody fragment is selected from the group consisting of an Fab' fragment, an F(ab')$_2$ fragment, or a single chain Fv fragment.

4. The method of claim 1, wherein said agent binds to B7-H4.

5. The method of claim 1, wherein said B7-H4 activity is decreased CD4$^+$ and CD8$^+$ T cell proliferation.

6. The method of claim 1, further comprising delivering to said patient one or more immunomodulatory cytokines, growth factors, or anti-angiogenic factors.

7. The method of claim 6, wherein said one or more immunomodulatory cytokines, growth factors, or anti-angiogenic factors are selected from the group consisting of interleukin (IL)-1 to 25, interferon-alpha (IFN-α), interferon-beta (IFN-β), interferon-gamma (IFN-γ), tumor necrosis factor-alpha (TNF-α), granulocyte macrophage colony stimulating factor (GM-CSF), endostatin, angiostatin, and thrombospondin.

8. The method of claim 1, wherein said patient has a cancer selected from the group consisting of hematological cancer, neurological cancer, melanoma, breast cancer, lung cancer, head and neck cancer, gastrointestinal cancer, liver cancer, pancreatic cancer, renal cancer, genitourinary cancer, bone cancer, and vascular cancer.

9. The method of claim 8, wherein said cancer is a renal cell carcinoma.

10. The method of claim 1, wherein said agent is an antisense oligonucleotide that hybridizes to a B7-H4 transcript.

11. The method of claim 1, wherein said agent is an interference RNA (RNAi).

* * * * *